(12) United States Patent
Rundle

(10) Patent No.: US 7,738,631 B2
(45) Date of Patent: Jun. 15, 2010

(54) ENERGY DISCRIMINATING SCATTER IMAGING SYSTEM

(75) Inventor: David S. Rundle, Butler, PA (US)

(73) Assignee: Endicott Interconnect Technologies, Inc., Endicott, NY (US)

( * ) Notice: Subject to any disclaimer, the term of this patent is extended or adjusted under 35 U.S.C. 154(b) by 40 days.

(21) Appl. No.: 11/916,591

(22) PCT Filed: Jun. 15, 2006

(86) PCT No.: PCT/US2006/023417

§ 371 (c)(1),
(2), (4) Date: Jun. 26, 2008

(87) PCT Pub. No.: WO2006/138521

PCT Pub. Date: Dec. 28, 2006

(65) Prior Publication Data

US 2008/0267353 A1   Oct. 30, 2008

Related U.S. Application Data

(60) Provisional application No. 60/691,045, filed on Jun. 16, 2005.

(51) Int. Cl.
*G01N 23/201* (2006.01)
*G01N 23/04* (2006.01)
*G01B 15/00* (2006.01)
*H01L 27/146* (2006.01)

(52) U.S. Cl. .............. 378/86; 378/57; 378/88; 378/90; 250/370.09; 250/370.13

(58) Field of Classification Search ............. 378/57, 378/70, 86, 87, 88, 90; 250/370.01, 370.08, 250/370.09, 370.12, 370.13
See application file for complete search history.

(56) References Cited

U.S. PATENT DOCUMENTS

| | | | |
|---|---|---|---|
| 4,047,029 A * | 9/1977 | Allport ........................ 378/90 |
| 4,884,289 A | 11/1989 | Glockmann et al. |
| 5,008,911 A | 4/1991 | Harding |
| 5,181,234 A | 1/1993 | Smith |
| 5,265,144 A * | 11/1993 | Harding et al. ............... 378/86 |
| 5,428,657 A * | 6/1995 | Papanicolopoulos et al. .. 378/86 |
| 5,600,700 A | 2/1997 | Krug et al. |
| 5,642,393 A * | 6/1997 | Krug et al. .................... 378/57 |
| 6,054,712 A | 4/2000 | Komardin et al. |
| 6,118,850 A * | 9/2000 | Mayo et al. .................... 378/83 |
| 6,399,951 B1 | 6/2002 | Paulus et al. |
| 6,532,276 B1 * | 3/2003 | Hartick et al. ................. 378/88 |
| 6,771,732 B2 * | 8/2004 | Xiao et al. ..................... 378/4 |
| 7,120,226 B2 * | 10/2006 | Ledoux et al. ................. 378/57 |
| 2001/0025928 A1 * | 10/2001 | Lingren et al. ......... 250/370.09 |
| 2003/0031295 A1 | 2/2003 | Harding |

(Continued)

*Primary Examiner*—Edward J Glick
*Assistant Examiner*—Anastasia Midkiff
(74) *Attorney, Agent, or Firm*—Mark Levy; Hinman, Howard & Kattell

(57) ABSTRACT

A specimen inspection system includes a photon source for outputting photons along a transmission path and a conveyor for translating a specimen completely through the transmission path. A radiation detector is positioned offset with respect to the transmission path for detecting photons that are scattered from the transmission path in response to interaction with the specimen passing therethrough. A controller determines from the detected scattered photons that a first material is present in the specimen.

20 Claims, 2 Drawing Sheets

U.S. PATENT DOCUMENTS

| | | | |
|---|---|---|---|
| 2004/0065838 A1* | 4/2004 | Tumer | 250/370.09 |
| 2004/0141585 A1 | 7/2004 | Proctor | |
| 2005/0053193 A1 | 3/2005 | Hasegawa | |
| 2005/0058242 A1 | 3/2005 | Peschmann | |
| 2005/0105685 A1 | 5/2005 | Harding | |
| 2005/0117700 A1 | 6/2005 | Peschmann | |
| 2006/0140340 A1* | 6/2006 | Kravis | 378/57 |
| 2009/0010381 A1 | 1/2009 | Schlomka | |

* cited by examiner

ENERGY DISCRIMINATING SCATTER IMAGING SYSTEM

CROSS REFERENCE TO RELATED APPLICATION

This application claims the benefit of U.S. Provisional Patent Application No. 60/691,045, filed Jun. 16, 2005, the contents of which are incorporated herein by reference.

BACKGROUND OF THE INVENTION

1. Field of the Invention

The present invention relates to specimen inspection systems and, more particularly, to specimen inspection systems that can discriminate between materials having similar densities.

2. Description of Related Art

The food inspection industry currently uses x-ray based systems that employ scintillator/photodiode linear arrays to verify portions and fill height, inspect food and packaging quality, identify food contaminants, and/or provide process control. These systems rely on the ability to detect the x-ray transmissive differences between food, packaging, and contaminants present. These systems are effective for inspecting products that have significantly different densities between the food product and the packaging or contaminant(s). However, where the contaminant(s) and/or packaging are similar in density to the food being inspected, the accuracy of the system to detect differences is compromised.

Accordingly, what is needed is an x-ray system and method of use thereof for use in the food inspection industry that can detect differences between the food being inspected and any contaminant(s) present in the food and/or the food packaging, especially where the contaminant(s) and/or packaging are similar in density to the food being inspected.

Examples of uses of x-rays for detecting differences between two or more constituent of a body can be found in the following articles: "The Potential for Compton Scattered X-rays in Food Inspection: The Effect of Multiple Scatter and Sample Inhomogeneity" by N. J. B. McFarlane, C. R. Bull, R. D. Tillett, R. D. Speller, G. J. Royle and K. R. A. Johnson, J. agric. Engng Res. (2000) 75, 265-274; "Energy-dispersive x-ray diffraction tomography" by G. Harding, M. Newton and J. Kosanetzky, Phys, Med. Biol., 1990, Vol. 35, No 1, 33-41; "Time Constraints on Glass Detection in Food Materials using Compton Scattered X-rays" by N. J. B. McFarlane, C. R. Bull, R. D. Tillett, R. D. Speller and G. J. Royle, J. agric. Engng, Res. (2001) 79(4), 407-418; and "Energy Dispersive X-ray Scatter for measurement of oil/water ratios", University of Surrey, Department of Physics Radiation Imaging, http://www.ph.surrey.ac.uk/rmm/imaging/xray_scatter/index.html.

SUMMARY OF THE INVENTION

The invention is a specimen inspection system. The system includes means for outputting photons along a transmission path and means for translating a specimen completely through the transmission path. A means for detecting photons that are scattered from the transmission path in response to interaction with the specimen passing therethrough is positioned offset with respect to the transmission path. Lastly, the system includes means for determining from the detected scattered photons that a first material is present in the specimen. The specimen is comprised of a plurality of materials, at least two of which, including the first material, block the passage of photons on the transmission path to approximately the same extent whereupon discrimination between said at least two materials based on photons exiting the specimen on the transmission path is prevented. The detected scattered photons are scattered in response to interaction with the first material.

The system can also include means positioned in the transmission path for detecting photons exiting the specimen on the transmission path.

The plurality of materials can include a second material that blocks the passage photons on the transmission path to a greater extent than the first material. The means for determining can determine from the detected photons that exit the specimen on the transmission path that the second material is present in the specimen.

The means for outputting photons can be an x-ray source. The first material can be plastic. The second material can be metal.

The means for detecting can detect at least one of coherent scattered photons and Compton scattered photons.

The means for detecting can include a first photon detector positioned at a first angle with respect to the transmission path. The means for detecting can also include a second photon detector positioned at a second angle with respect to the transmission path. The first and second detectors can be positioned to detect coherent and Compton scattered photons, respectively.

The means for detecting can include a linear array of photon detectors operable at room temperature. The linear array of photon detectors can include a core material that produces electron-hole pairs in response to interaction with incident photons, a first electrode positioned on one surface of said core material, and a plurality of second electrodes positioned on another surface of said core material opposite said first electrode.

The core material can include Cadmium Telluride or Cadmium Zinc Telluride.

The invention is also a method of specimen inspection comprising (a) outputting photons along a transmission path; (b) translating a specimen completely through the transmission path; (c) detecting photons that are scattered from the transmission path in response to interaction with the specimen passing therethrough; and (d) determining from the detected scattered photons that a first material is present in the specimen. The specimen is comprised of at least two materials that block the passage of photons on the transmission path to approximately the same extent whereupon discrimination between said at least two materials based on photons exiting the specimen on the transmission path is prevented. The detected scattered photons are scattered in response to interaction with the first material of said at least two materials.

The method can further include detecting photons exiting the specimen on the transmission path and determining from the detected photons that exit the specimen on the transmission path that the second material of said at least two materials, that blocks the passage photons on the transmission path to a greater extent than the first material, is present in the specimen.

Step (c) can include detecting coherent scattered photons and/or Compton scattered photons.

Lastly, the invention is a specimen inspection system. The system includes a combination radiation source and collimator for outputting photons along a fan shaped transmission path and a photon detector positioned offset with respect to the transmission path for detecting photons that are scattered from the transmission path in response to interaction with a slice of a specimen defined by and disposed completely in the transmission path. Means is provided for determining from the detected scattered photons that a first material is present in the specimen which is comprised of the first material and a second material that block the passage of photons on the transmission path to approximately the same extent whereupon discrimination between the first and second materials based on photons exiting the specimen on the transmission path is prevented. The detected scattered photons are scattered in response to interaction with the first material.

Another photon detector can be positioned in the transmission path for detecting photons exiting the specimen on the transmission path.

The second material blocks the passage photons on the transmission path to a greater extent than the first material and the means for determining determines from the detected photons that exit the specimen on the transmission path that the second material is present in the specimen.

The photon detector can be positioned at a first angle with respect to the transmission path for detecting at least one of coherent scattered photons and Compton scattered photons. The system can also include another photon detector positioned at a second angle with respect to the transmission path.

DETAILED DESCRIPTION OF THE INVENTION

The present invention will described with reference to the accompanying figures where like reference numbers correspond to like elements.

Figure 1:
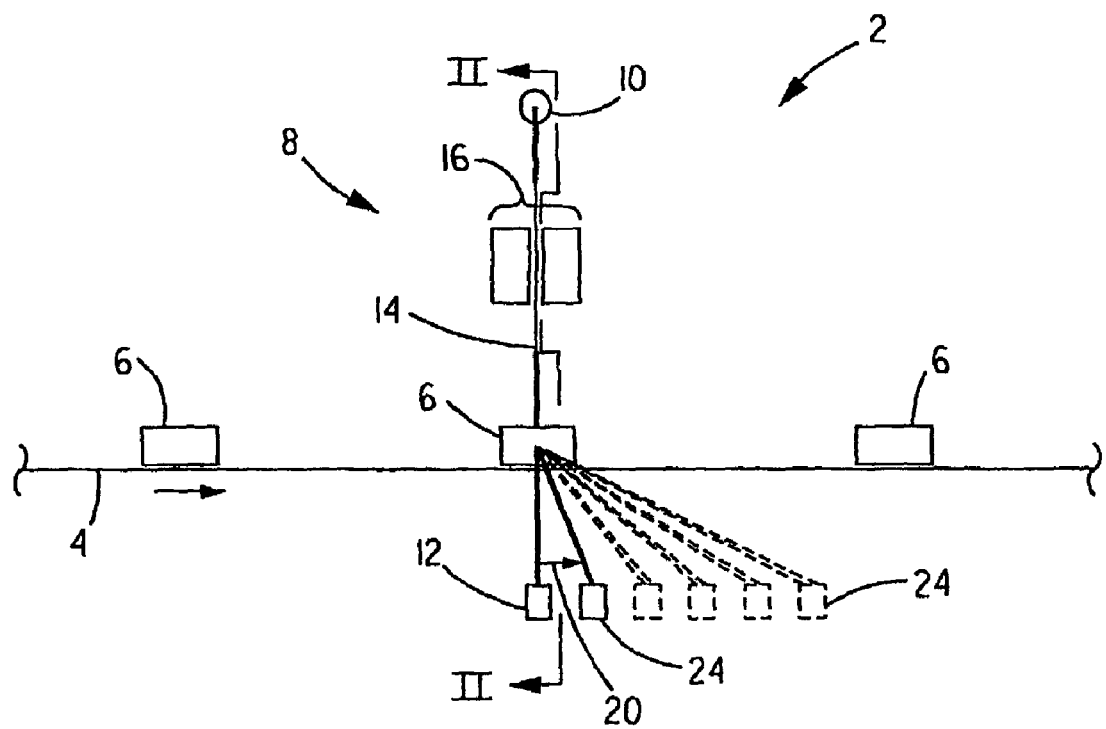
FIG. 1 is a side schematic view of a specimen inspection system in accordance with the present invention.

With reference to FIG. 1, the present invention is a specimen inspection system 2 that includes a conveyor belt 4 for translating a specimen, such as packaged or unpackaged food product 6, through an inspection station 8. The present invention will be described with reference to the specimen being food product 6. However, this is not to be construed as limiting the invention.

Figure 2:
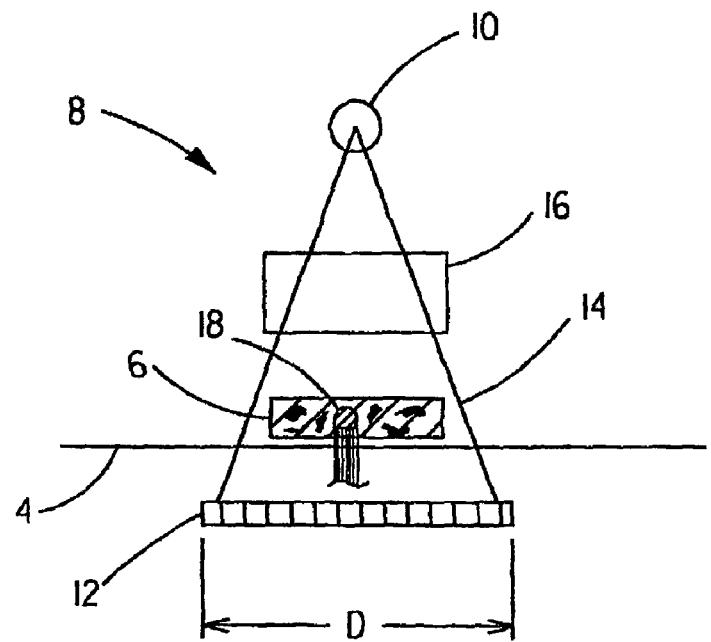
FIG. 2 is a section taken along line II-II in FIG. 1.

With reference to FIG. 2, and with continuing reference to FIG. 1, inspection station 8 includes a high energy photon source 10, such as, without limitation, an x-ray source, and at least one linear photon detector array 12 positioned on opposite sides of conveyor belt 4. In FIG. 1, photon source 10 and detector array 12 are shown positioned above and below, respectively, conveyor belt 4. However, this is not to be construed as limiting the invention since the locations of photon source 10 and detector array 12 can be reversed if desired.

Detector array 12 is desirably positioned in a transmission path 14 of photons output by photon source 10. For purpose of food inspection, transmission path 14 is desirably fan shaped (shown best in FIG. 2) whereupon each part of food product 6 translated by conveyor belt 4 passes completely through transmission path 14 during inspection of food product 6. More specifically, the interaction between transmission path 14 and each part of food product 6 being translated therethrough defines a slice of food product 6 under test. As would be appreciated, continuous translation of food product 6 completely through transmission path 14 defines a series of continuous slices of food product 6 under test. Food product 6 can either be in the form of one or more discreet masses of food product 6, as shown in FIG. 1, or a continuous mass of food product 6 on conveyor belt 4.

In order to shape and focus transmission path 14, inspection station 8 can include a collimator means 16 positioned between photon source 10 and conveyor belt 4 for collimating transmission path 14 before it is utilized for inspecting food product 6 on conveyor belt 4.

Collimator means 16 can take on any suitable or desirable form. For example, collimator means 16 can include one or more full collimators; one or more full collimators in combination with one or more half collimators; and the like. The choice of one or more collimators to form collimator means 16 can be made by one of ordinary skill in the art based upon the desired degree of collimation required.

Depending upon the application, linear detector array 12 has a length D between 2 inches and 10 inches. However, this is not to be construed as limiting the invention since the length D of detector array 12 can be selected by one of ordinary skill in the art to be any suitable and/or desirable length for the application.

A particularly difficult contaminant 18 to detect in food product 6 is plastic. For example, it is particularly difficult to detect a piece of plastic contaminant 18 in a volume of food product 6, e.g., meat, based on photons traveling along transmission path 14 and received by detector array 12. However, photon scattering may be utilized as a basis for detecting contaminant 18 in food product 6.

Photon scattering may be classified into two general categories, namely, (1) coherent or elastic scattering and (2) Compton or inelastic scattering. With respect to the direction of transmission path 14, coherent scattering of photons at energies between 10-40 keV interacting with contaminant 18 typically occurs at angles 20 less than or equal to 10° with respect to transmission path 14. In contrast, Compton scattering at energies between 10-40 keV typically occurs at angles 20 greater than 40° with respect to transmission path 14. Photon scattering at an angles 20 between 10° and 40° with respect to transmission path 14 is considered to be a combination of coherent and Compton scattering. Inasmuch as the angle that each scattered photon is scattered is dependent upon the incident energy of the photon, the foregoing angles are not to be construed as limiting the invention.

In accordance with the present invention, the presence of contaminant 18 in food product 6 can be detected by one or more linear detector arrays 24, like linear detector array 12, positioned at one or more different angles 20 with respect to transmission path 14 to detect coherent scattering, Compton scattering and/or combinations thereof caused by interaction between photons traveling on transmission path 14 and contaminant 18 in food product 6.

For example, in addition to detector array 12, another single detector array 24 can be positioned to detect coherent scattering or Compton scattering. Alternatively, instead of one single detector array 24, a pair of detector arrays 24 can be provided, with one of said pair of detector arrays 24 positioned to detect coherent scattering and with the other of said pair of detector arrays 24 positioned to detect Compton scattering. Alternatively, more than two detector arrays 24 can be provided for detecting any combination of coherent scattering, Compton scattering and/or Compton/coherent scattering.

The angle 20 that a single detector array 24 or each of a plurality of detector arrays 24 are positioned with respect to transmission path 14 can be optimized for a particular type of contaminant 18 to be detected and photon energy. For example, at photon energies between 10 and 40 keV, a single detector array 24 can be positioned at angle 20 between 1° and 20°, desirably between 5° and 10°, of transmission path 14 for detecting coherent scattering, can be positioned between 40° 60°, desirably between 45° and 55°, of transmission path 14 for detecting Compton scattering, or can be positioned between 20° and 40°, desirably between 25° and 30°, of transmission path 14 for detecting the combination of Compton and coherent scattering. Alternatively, a first detector array 24 can be positioned at an angle 20 between 1° and 20°, desirably between, 5° and 10°, of transmission path 14 to detect coherent scattering while a second detector array 24 can be positioned at an angle 20 between 40° and 60°, desirably between 45° and 55°, of transmission path 14 to detect Compton scattering. In addition, if desired, a third detector array 24 can be positioned at an angle 20 between 20° and 40°, desirably between 25° and 30°, of transmission path 14 for detecting the combination of Compton and coherent scattering.

The number of detector arrays and the angle 20 that each detector array is positioned with respect to transmission path 14 can be selected as needed for detecting contaminant 18 in food product 6 based on the contaminant 18 being detected and/or the photon energy of the photons being generated by photon source 10 on transmission path 14. Accordingly, the number of detector arrays 24 and the positioning of each detector array 24 at a suitable angle 20 described above is not to be construed as limiting the invention.

Figure 3:
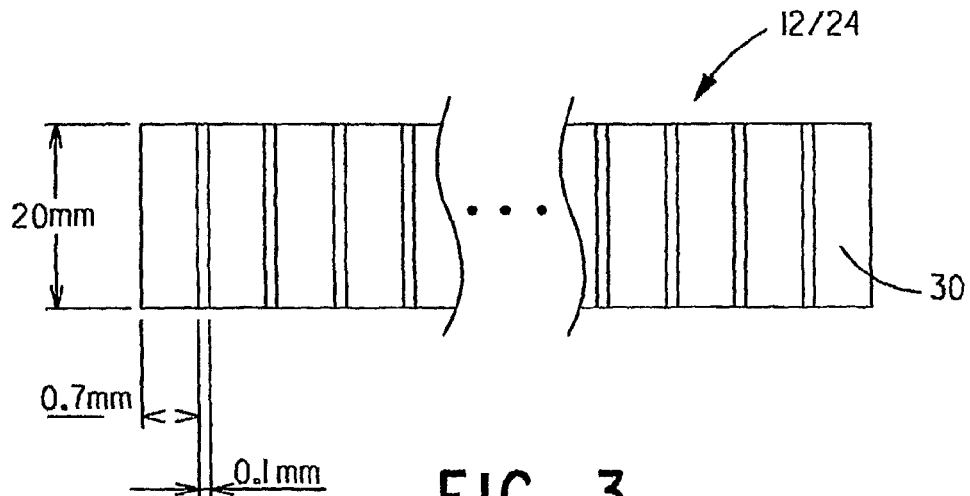
FIG. 3 is a plan view of the anode side of an exemplary detector array shown in FIGS. 1 and 2.
Figure 4:
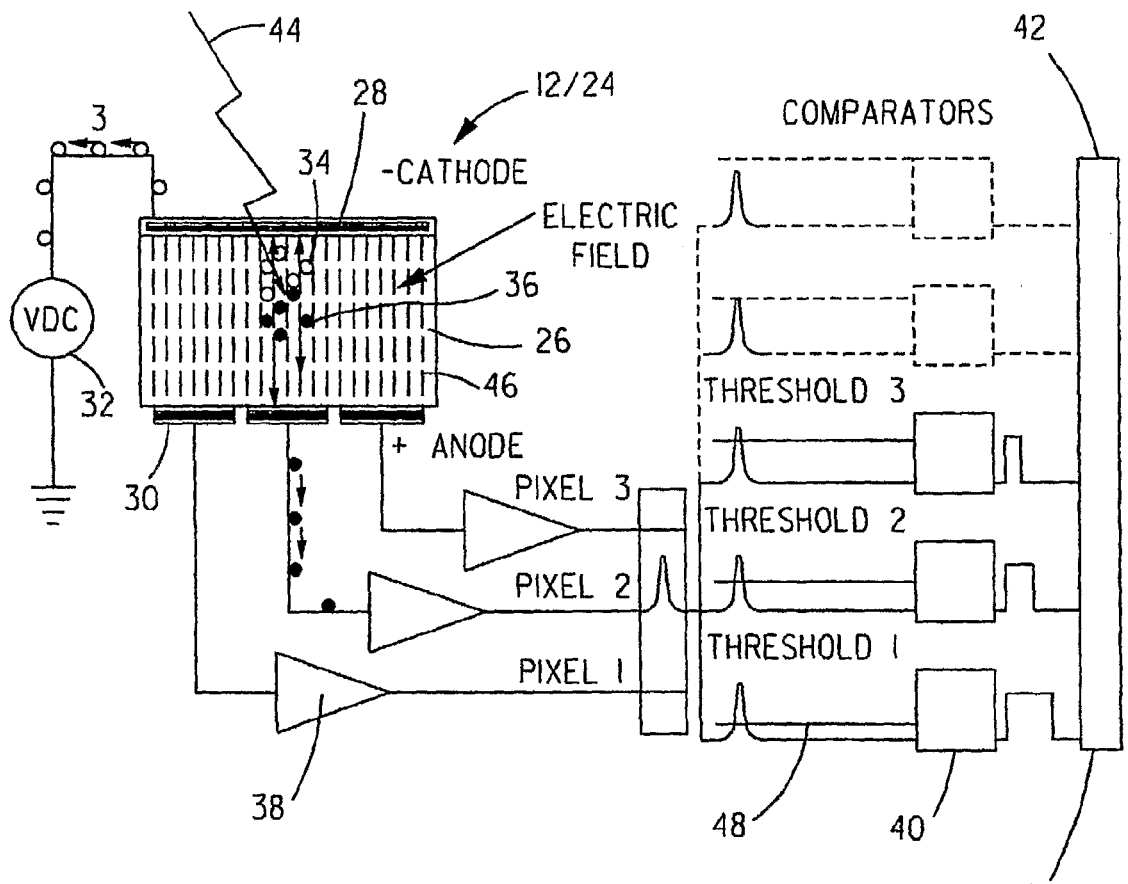
FIG. 4 is a side view of an exemplary detector array coupled to a block diagram of a circuit utilized to bias the detector array and to detect and store counts of energy levels of photons interacting with a core material of the detector array.

With reference to FIGS. 3 and 4, each detector array 12 and 24 is desirably a room temperature semiconductor linear array. Each detector array 12 and 24 includes a core material 26 formed of a material, such as Cadmium Telluride (CT) or Cadmium Zinc Telluride (CZT), that generates electron-hole pairs in response to a high energy photon interacting with a crystal lattice structure thereof. Each detector array 12 and 24 includes a continuous cathode 28 on the photon entry side thereof and a plurality of segmented anodes 30 on a side of core material 26 opposite cathode 28. Cathode 28 is coupled to a voltage source 32 which biases cathode 28 to a suitable potential relative to anodes 30 whereupon holes created in core material 26 are attracted to cathode 28 and electrons 36 generated in core material 26 are attracted toward one or more anodes 30.

FIG. 3 includes dimensions of an exemplary detector array 12 or 24. The dimensions shown in FIG. 3, however, are not to be construed as limiting the invention.

Each anode 30 represents a picture element (or pixel) of detector array 12 or 24. Each anode 30 is connected to a charge sensitive amplifier 38. The output of each amplifier 38 is a semi-Gaussian shaped signal with a height that is proportional to the incident photon energy. The output of each amplifier 38 is connected to one or more comparators, each of which has a preset threshold to determine the energy of the incident photon. The output of each comparator is coupled to a controller 42 which is operative for sampling the output of each comparator 40 and for determining therefrom the energy of the incident photon.

In operation, when a photon 44 interacts with core material 26, a plurality of electron-hole pairs is created that is proportional to the energy of said photon 44. Under the influence of an electric field 46 produced in core material 26 in response to the application of a suitable electrical bias between cathode 28 and each anode 30 by voltage source 32, electrons 36 and holes 34 migrate to anodes 30 and cathode 28, respectively. The electrons reaching each anode 30 are amplified by the corresponding amplifier 38 to produce the semi-Gaussain shaped signal. This signal is input into one or more comparators 40, each of which has a different preset threshold value 48. Each comparator is configured to output a signal having a duration corresponding to the time the semi-Gaussain shaped signal output by the corresponding amplifier 38 exceeds the corresponding threshold 48. At suitable times, controller 42 samples the output of each comparator 40 and determines therefrom the energy of the incident photon in a manner known in the art.

Controller 42 can be operative to accumulate counts of incident photons having a number of different energy levels. Thus, for example, if the output of each amplifier 38 is coupled to the inputs of a plurality of comparators 40, each of which has a different threshold corresponding to a different energy of an incident photon, in response to detecting that the signal output by one of the amplifiers 38 exceeds a first threshold, but not a second threshold, controller 42 can increment a counter associated with the first threshold as a record of the energy of the incident photon. Thus, if three comparators have their respective thresholds set to detect signal amplitudes exceeding corresponding photon energy levels of 15 keV, 30 keV and 40 keV, controller 42 can accumulate a count of each signal amplitude as a function of the photon energy level it represents. For example, if a signal amplitude exceeds the threshold 48 corresponding to 15 KeV, but does not exceed the threshold 48 corresponding to 30 keV, controller 42 increments the value of a first counter established to maintain a count of signal amplitudes that exceed the threshold 48 corresponding to 15 keV but which do not exceed the threshold 48 corresponding to 30 keV. Similarly, each signal amplitude that exceeds the threshold 48 corresponding to 30 keV causes controller 42 to increment only the value of a counter established for maintaining a count of signal amplitudes that exceed the threshold 48 corresponding to 30 keV but which do not exceed the threshold 48 corresponding to 40 keV. When a signal amplitude exceeds the threshold 48 corresponding to 30 keV, controller 42 is operative for not incrementing the value of a counter established for maintaining a count of signal amplitudes that exceed the threshold 48 corresponding to 15 keV, even though the output of the corresponding comparator 40 indicates that its corresponding threshold 48 has been exceeded. Lastly, for each signal amplitude that exceeds the threshold 48 corresponding to 40 keV, controller 42 increments only the value of a counter established for maintaining a count of the number of signal amplitudes that exceed the threshold 48 corresponding to 40 keV. When a signal amplitude exceeds the threshold 48 corresponding to 40 keV, controller 42 is operative for not incrementing the value of the counters established for maintaining a count of signal amplitudes that exceed the thresholds 48 corresponding to 15 and 30 keV, even though the outputs of the corresponding comparators 40 indicate that their corresponding thresholds 48 have been exceeded.

Obviously, if more resolution is desired, one or more additional comparators 40 having different thresholds 48 can be provided.

Once a suitable number of counts for a suitable duration of time have been accumulated, controller 42 can output these counts to an image processing system (not shown) for processing in a manner known in the art.

Importantly, in accordance with the present invention, energy binning can be performed for photons that travel on transmission path 14 and are detected by detector array 12 as well as on scattered photons detected by one or more detector arrays 24, each of which is positioned at a suitable angle 20 with respect to transmission path 14.

The ability to classify the energy of scattered photons interacting with the core material 26 of a detector array 24 facilitates accurate identification of one or more contaminants 18 in food product 6.

As can be seen, by proper placement of a detector array 24 at a suitable angle 20 with respect to transmission path 14, said detector array 24 can detect for the presence of one or more contaminants in a food product. The energy of scattered photons impinging upon said detector array 24 can be determined and placed into bins which can be utilized to further facilitate identification of the one or more contaminants in the food product. A plurality of detector arrays 24, each of which is placed at a different angle 20 with respect to transmission path 14, can also be utilized for detecting for the presence of one or more contaminants in food product.

Each detector array 24 can be utilized in combination with detector array 12 positioned in transmission path 14. However, this is not to be construed as limiting the invention since detector array 12 can be omitted and one or more detector arrays 24 can be positioned as discussed above to detect scattered photons.

The present invention has been described with reference to the preferred embodiments. Obvious modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A specimen inspection system comprising:
means for outputting photons along a transmission path;
means for translating a specimen completely through the transmission path;
a first set of photon detectors positioned at a first angle with respect to the transmission path;
a second set of photon detectors positioned at a second angle with respect to the transmission path, wherein:
the first and second sets of photon detectors are positioned to detect coherent and Compton scattered photons, respectively, scattered from the transmission path in response to interaction with the specimen passing therethrough, wherein the coherent and/or Compton scattered photons do not pass through a collimator prior to detecting the scattered photons by the first and/or second sets of photon detectors, respectively; and
means for determining from the detected scattered photons that a first material is present in the specimen, wherein:
the specimen comprises a plurality of material at least two of said plurality of materials, including the first material, block the passage of photons on the transmission path to approximately the same extent whereupon discrimination between said at least two materials based on photons exiting the specimen on the transmission path is prevented; and
the detected scattered photons are scattered in response to interaction with the first material.

2. The system of claim 1, further including means positioned in the transmission path for detecting photons exiting the specimen on the transmission path.

3. The system of claim 2, wherein:
the plurality of materials includes a second material that blocks the passage of photons on the transmission path to a greater extent than does the first material; and
the means for determining determines, from the detected scattered photons that exit the specimen on the transmission path, that the second material is present in the specimen.

4. The system of claim 3, wherein:
the means for outputting photons is an x-ray source;
the first material is plastic; and
the second material is metal.

5. The system of claim 1, wherein:
the first set of photon detectors comprises a first linear array of photon detectors operable at room temperature; and
the second set of photon detectors comprises a second linear array of photon detectors operable at room temperature.

6. The system of claim 5, wherein the first and second linear arrays of photon detectors comprise:
a core material that produces electron-hole pairs in response to interaction with incident photons;
a first electrode positioned on one surface of said core material; and
a plurality of second electrodes positioned on another surface of said core material opposite said first electrode.

7. The system of claim 6, wherein the core material is comprised of either Cadmium Telluride or Cadmium Zinc Telluride.

8. The system of claim 1, wherein:
said first angle is between approximately 1 and 20 degrees; and
said second angle is between approximately 40 and 60 degrees.

9. A method of specimen inspection comprising:
a) outputting photons along a transmission path;
b) translating a specimen completely through the transmission path;
c) detecting coherent scattered photons scattered from the transmission path in response to interaction with the specimen passing therethrough;
d) detecting Compton scattered photons scattered from the transmission path in response to interaction with the specimen passing therethrough;
e) wherein the photons scattered in said steps (c) and/or (d) are detected without passage of said scattered photons through a collimator; and
f) determining from the detected scattered photons that a first material is present in the specimen, wherein:
the specimen comprises a plurality of materials;
at least two of said plurality of materials, including the first material, block the passage of photons on the transmission path to approximately the same extent whereupon discrimination between said at least two materials based on photons exiting the specimen on the transmission path is prevented; and
the detected scattered photons are scattered in response to interaction with the first material.

10. The method of claim 9, further including detecting photons exiting the specimen on the transmission path.

11. The method of claim 10, further including determining from the detected photons that exit the specimen on the transmission path that a second material, that blocks the passage photons on the transmission path to a greater extent than the first material, is present in the specimen.

12. The method of claim 9, further including detecting any combination of coherent and Compton scattered photons scattered from the transmission path in response to interaction with the specimen passing therethrough.

13. A specimen inspection system comprising:
a combination radiation source and collimator for outputting photons along a fan shaped transmission path;
a first set of photon detectors positioned at a first angle with respect to the transmission path for detecting photons scattered from the transmission path in response to interaction with a slice of a specimen defined by and disposed completely in the transmission path;
a second set of photon detectors positioned at a second angle with respect to the transmission path for detecting photons scattered from the transmission path in response to interaction with a slice of a specimen defined by and disposed completely in the transmission path; wherein:
the first and second sets of photon detectors are positioned to detect coherent and Compton scattered photons, respectively, wherein the coherent and/or Compton scattered photons do not pass through a collimator prior to detecting the scattered photons by the first and/or second sets of photon detectors, respectively; and
means for determining from the detected scattered photons that a first material is present in the specimen, wherein:
the specimen comprises the first material and a second material that block the passage of photons on the transmission path to approximately the same extent whereupon discrimination between the first and second materials based on photons exiting the specimen on the transmission path is prevented; and
the detected scattered photons are scattered in response to interaction with the first material.

14. The system of claim 13, further including at least one other photon detector positioned in the transmission path for detecting photons exiting the specimen on the transmission path.

15. The system of claim 14, wherein:
the second material blocks the passage of photons on the transmission path to a greater extent than does the first material; and
the means for determining determines, from the detected photons that exit the specimen on the transmission path, that the second material is present in the specimen.

16. The system of claim 13, wherein:
said first angle is between approximately 1 and 20 degrees; and
said second angle is between approximately 40 and 60 degrees.

17. A specimen inspection system comprising:
a) means for outputting photons along a transmission path;
b) means for translating a specimen completely through the transmission path;
c) a first set of photon detectors positioned at a first angle with respect to the transmission path;
d) a second set of photon detectors positioned at a second angle with respect to the transmission path, wherein:
the first and second sets of photon detectors are positioned to detect coherent and Compton scattered photons, respectively, scattered from the transmission path in response to interaction with the specimen passing therethrough;
means for determining from the detected scattered photons that a first material is present in the specimen, wherein:
the specimen comprises a plurality of materials;
at least two of said plurality of materials, including the first material, block the passage of photons on the transmission path to approximately the same extent whereupon discrimination between said at least two materials based on photons exiting the specimen on the transmission path is prevented;
the detected scattered photons are scattered in response to interaction with the first material; and
e) a third set of photon detectors positioned at a third angle with respect to the transmission path, to detect any combination of coherent and Compton scattered photons.

18. The system of claim 17, wherein said third angle is between approximately 20 and 40 degrees.

19. A specimen inspection system comprising:
a) a combination radiation source and collimator for outputting photons along a fan shaped transmission path;
b) a first set of photon detectors positioned at a first angle with respect to the transmission path for detecting photons scattered from the transmission path in response to interaction with a slice of a specimen defined by and disposed completely in the transmission path;
c) a second set of photon detectors positioned at a second angle with respect to the transmission path for detecting photons scattered from the transmission path in response to interaction with a slice of a specimen defined by and disposed completely in the transmission path; wherein:
the first and second sets of photon detectors are positioned to detect coherent and Compton scattered photons, respectively; and
means for determining from the detected scattered photons that a first material is present in the specimen, wherein:
the specimen comprises the first material and a second material that block the passage of photons on the transmission path to approximately the same extent whereupon discrimination between the first and second materials based on photons exiting the specimen on the transmission path is prevented;
the detected scattered photons are scattered in response to interaction with the first material; and
d) a third set of photon detectors positioned at a third angle with respect to the transmission path, to detect any combination of coherent and Compton scattered photons.

20. The system of claim 19, wherein said third angle is between approximately 20 and 40 degrees.

* * * * *